United States Patent [19]

Forestier et al.

[11] Patent Number: 5,302,376
[45] Date of Patent: Apr. 12, 1994

[54] COSMETIC SCREENING EMULSION COMPRISING A UV-A SCREENING AGENT AND A UV-B SCREENING AGENT AND ITS USE FOR SKIN PROTECTION AGAINST ULTRAVIOLET RADIATION

[75] Inventors: Serge Forestier, Claye-Souilly; Martine Eteve, Paris, both of France

[73] Assignee: L'Oreal, Paris, France

[21] Appl. No.: 696,784

[22] Filed: May 7, 1991

[30] Foreign Application Priority Data

May 18, 1990 [FR] France ................................. 90 06278

[51] Int. Cl.$^5$ ......................... A61K 7/42; A61K 7/44; A61K 9/10; A61K 9/12
[52] U.S. Cl. ......................................... 424/59; 424/47; 424/60; 514/938
[58] Field of Search ............................. 424/60, 59, 47

[56] References Cited

U.S. PATENT DOCUMENTS

| | | | |
|---|---|---|---|
| 3,278,534 | 10/1966 | Schellenbaum et al. | 424/59 |
| 4,724,137 | 2/1988 | Hoppe et al. | 424/59 |
| 4,929,439 | 5/1990 | Cotteret et al. | 424/59 |
| 4,985,237 | 1/1991 | Matsuno et al. | 424/59 |
| 5,004,594 | 4/1991 | Richard et al. | 424/DIG. 5 |

FOREIGN PATENT DOCUMENTS

| | | | |
|---|---|---|---|
| 0087098 | 8/1983 | European Pat. Off. | 424/59 |
| 0365370 | 4/1990 | European Pat. Off. | 424/59 |
| 2121801 | 1/1984 | United Kingdom | 424/59 |

Primary Examiner—Dale R. Ore
Attorney, Agent, or Firm—Jacobson, Price, Holman & Stern

[57] ABSTRACT

The invention relates to a cosmetic emulsion screening out UV radiation of wavelengths between 280 and 400 nm comprising in the oil phase, 2,4,6-tris[[p-(2'-ethylhexyl-1'-oxycarbonyl)anilino]-1,3,5-triazine and, in the aqueous phase, benzene-1,4-[bis(3-methylidenecamphormethylsulphonic)] acid, partially or completely neutralised, of formula:

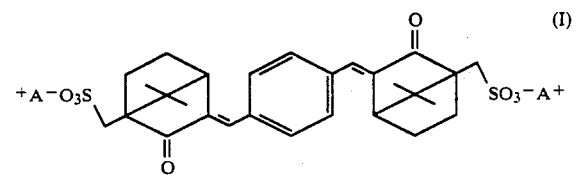

in which A designates a hydrogen atom, an alkali metal, a $N(R)_4^+$ group, R designating a hydrogen atom or a $C_1$-$C_4$ alkyl or hydroxyalkyl radical, or a $M^{n+}/n$ group where $M^{n+}$ is a polyvalent metal cation in which n is equal to 2 or 3 or 4, $M^{n+}$ preferably designating $Ca^{2+}$, $Zn^{2+}$, $Mg^{2+}$, $Ba^{2+}$, $Al^{3+}$ or $Zr^{4+}$.

The cosmetic screening emulsion according to the invention possesses an improved protection index.

15 Claims, No Drawings

COSMETIC SCREENING EMULSION COMPRISING A UV-A SCREENING AGENT AND A UV-B SCREENING AGENT AND ITS USE FOR SKIN PROTECTION AGAINST ULTRAVIOLET RADIATION

The present invention relates to a cosmetic composition screening out ultraviolet radiation, in emulsion form comprising, in combination, a hydrophilic UV-A screen and a lipophilic UV-B screen selected so as to increase the protection index of the said composition, as well as the use of the said composition for protecting the human epidermis against ultraviolet radiation.

It is known that light radiation of wavelengths between 280 and 400 nm allow tanning of the human epidermis and that rays of wavelengths between 280 and 320 nm known under the name of UV-B also cause erythemas and skin burns which can compromise the development of a tan.

However, although UV-B rays of wavelengths between 280 and 320 nm play a predominant role in the production of solar erythema and must be screened, it is true nevertheless that UV-A rays of wavelengths between 320 and 400 nm which cause tanning of the skin are also likely to induce modification of the latter, especially in the case of sensitive skin or skin continually exposed to solar radiation. UV-A rays cause in particular loss of elasticity of the skin and the appearance of wrinkles leading to early ageing. They promote the appearance of the erythematous reaction or amplify this reaction in some individuals and may even be the cause of phototoxic or photoallergic reactions.

It may therefore be advantageous to screen all the radiation of wavelengths between 280 and 400 nm.

Thus, the use of active compounds strongly absorbing UV rays over a broad range has already been proposed among which, more particularly, are benzene[bis(methylidenecamphor)] derivatives sulphonated on the methyl radical in position 10 of the camphor such as described in the French Patent No. 2 528 420 by the Applicant. These screens strongly absorb UV rays of wavelengths between 280 and 400 nm with absorption maxima between 320 and 400 nm for the compounds with methylidenecamphor radicals in the para position with respect to the benzene ring, and especially in the region of 345 nm.

The efficacy of cosmetic compositions containing these large spectrum UV screens, expressed by the sun-protection factor which is generally called "protection index or PI", is good, but it is as yet insufficient for very sensitive skins or for skins continually exposed to solar radiation, especially in the case of the UV-B protection index.

The protection index or PI may be expressed as the ratio of the irradiation time required to reach the erythematogenic threshold with the UV screen to the irradiation time required to reach the erythematogenic threshold without UV screen.

The use of triazine derivatives such as those described in the American Patent US 4 724 137 and more particularly 2,4,6-tris[p-(2'-ethylhexyl-1'-oxycarbonyl)-anilino]-1,3,5-triazine has also been proposed. These screens strongly absorb UV rays of wavelengths between 280 nm and 320 nm with an absorption maximum at 312 nm.

However, the protection index of cosmetic compositions containing the latter screen is also as yet insufficient in the case of extremely sensitive skins.

Moreover, at the industrial level, it is obviously advantageous to have UV screens which allow, at low concentrations, sun-protection compositions of high protection index to be obtained.

The Applicant has just discovered that by combining in an emulsion, the benzene[bis(methylidenecamphor)]derivative sulphonated on the methyl radical in position 10 of the camphor consisting of benzene-1,4-[bis(3-methylidenecamphormethylsulphonic)]acid or its aqueous-medium soluble or dispersible salts, which is a UV-A screen with an absorption maximum in the region of 345 nm, with 2,4,6-tris-[p-(2'-ethylhexyl-1'-oxycarbonyl)anilino]-1,3,5-triazine, which is a UV-B screen with an absorption maximum at 312 nm, there is obtained, surprisingly, for an emulsion containing a given concentration of the two aforementioned screens taken in combination, a protection index, especially UV-B, substantially higher than the protection indices of emulsions containing one or the other of these two screens at the same concentration and in the same carrier.

The subject of the present invention is therefore a cosmetic emulsion screening out ultraviolet radiation of wavelengths between 280 and 400 nm containing, in an aqueous phase, benzene-1,4-[bis(3-methylidenecamphormethylsulphonic)]acid, partially or completely neutralised, of formula (I) below, in combination with 2,4,6-tris[p-(2'-ethylhexyl-1'-oxycarbonyl]anilino]-1,3,5-triazine, in the oil phase.

Benzene-1,4-[bis(3-methylidenecamphormethylsulphonic)]acid, partially or completely neutralised, is of the formula

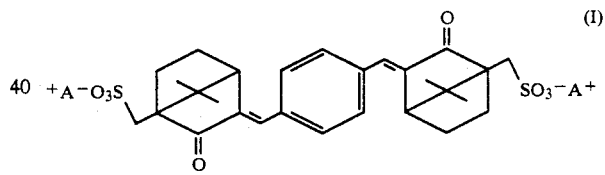

(I)

in which A designates a hydrogen atom, an alkali metal, a $N(R)_4^+$ group, R designating a hydrogen atom or a $C_1$-$C_4$ alkyl or hydroxyalkyl radical, or a $M^{n+}/n$ group where $M^{n+}$ is a polyvalent metal cation in which n is equal to 2 or 3 or 4, $M^{n+}$ preferably designating $Ca^{2+}$, $Zn^{2+}$, $Mg^{2+}$, $Ba^{2+}$, $Al^{3+}$ or $Zr^{4+}$.

Naturally, the compound of formula (I) may give rise to the "cis-trans" isomer around one or more double bonds and all the isomers are part of the invention.

The subject of the present invention is also a process for protecting the human epidermis against ultraviolet radiation of wavelengths between 280 and 400 nm, which consists in applying to the skin an efficacious quantity of the aforementioned cosmetic screening composition in the form of an emulsion comprising, in combination, benzene-1,4-[bis(3-methylidenecamphormethylsulphonic)] acid, partially or completely neutralised, and 2,4,6-tris[p-(2'-ethylhexyl-1'-oxycarbonyl)anilino]-1,3,5-triazine.

The cosmetic screening composition according to the invention has, in addition to its high protection index, the advantage of being thermally and photochemically stable, of not being toxic and of being perfectly harmless for the skin.

Moreover, this cosmetic composition does not feel sticky, does not allow a whitish film to remain on the skin after application and also exhibits a high persistence.

The persistence may be defined as the protection index stability of the screening composition during sun exposure. It is important that this persistence be high because it is necessary that the protection index be constant during exposure, which allows avoidance of repeated applications at regular and close intervals often necessary to obtain an effective protection of the skin against UV rays.

This protection index may vary either because the screen is photochemically unstable, or because it penetrates into the skin and no longer fulfills its role, or because it is eliminated during bathing.

2,4,6-Tris[p-(2'-ethylhexyl-1'-oxycarbonyl)anilino]-1,3,5-triazine is sold by the company BASF under the commercial name UVINUL T 150.

The following may be used to neutralise benzene-1,4-[bis(3-methylidenecamphormethylsulphonic)] acid: alkaline hydroxides and more particularly of sodium or potassium, ammonium hydroxide, alkanolamines, triethanolamine being preferred. Water-soluble alkali metal, ammonium or amine salts are thus obtained.

To obtain the water insoluble polyvalent metal salts of formula (I) in which A designates a polyvalent metal cation $M^{n+}$ of valency equal to 2, 3 or 4, a corresponding polyvalent metal salt or hydroxide, optionally in solution or in aqueous suspension, is added to an aqueous solution of a compound of formula (I) in which A designates a hydrogen atom, an alkali metal such as sodium or potassium or an ammonium residue.

The polyvalent metal salt may be for example a halide, in particular a bromide or a chloride, a nitrate, an acetate, a carbonate or a sulphate.

The addition of the polyvalent metal salt is carried out under stirring. When the compound of formula (I) is in the sulphonic acid form, the pH of the reaction mixture may optionally be adjusted to around neutrality during the course of the reaction by addition of an aqueous solution of an alkali metal or ammonium hydroxide.

This reaction may also be performed by inversing the order in which agents are introduced.

The polyvalent metal salt is preferably used in a stoichiometric amount to salify the initial compound of formula (I).

The compound of formula (I) in which A designates a polyvalent metal cation $M^{n+}$, precipitates during the reaction. It is separated by filtration, then washed with water to remove the inorganic salts.

The compound of formula (I) in acid form or in the form of an alkali metal, ammonium or amine salt may be prepared according to the procedures described in the Patent FR-2 528 420.

By way of compounds (I) in which A designates $M^{n+}/n$ which are preferred in particular, the compounds in which $M^{n+}$ designates $Ca^{2+}$, $Zn^{2+}$, $Mg^{2+}$, $Al^{3+}$ or $Zr^{4+}$ may be mentioned.

The sun-protection emulsions according to the invention contain, in the aqueous phase, benzene-1,4-[bis(3-methylidenecamphorsulphonic] acid, partially or completely neutralised, which is a hydrophilic compound; it is used in proportions, calculated on the basis of the acid, between 0.1 and 10% by weight, and preferably between 1 and 6% relative to the total weight of the composition.

The sun-protection emulsions according to the invention contain, in the oil phase, UVINUL T 150, which is a lipophilic compound, in proportions between 0.1 and 10% by weight, and preferably between 1 and 6% relative to the total weight of the composition.

In the case of oil/water (O/W) emulsions, the pH is between 4 and 9 and preferably between 5.5 and 8. It may be adjusted using the usual alkalising or acidifying agents.

The oil phase consists of fatty substances such as:
mineral oils such as liquid paraffin;
vegetable or animal oils, modified or not, such as sweet almond nut oil, avocado oil, calophyllum oil, castor oil, olive oil, lanolin and its derivatives, perhydrosqualene, groundnut oil, wheatgerm oil, linseed oil, jojoba oil, apricot stone oil, nut oil, palm oil, pistachio nut oil, sesame oil, rapeseed oil, cade oil, maize germ oil, peach stone oil, poppyseed oil, pine oil, soybean oil, safflower oil, coconut oil, hazelnut oil, grapeseed oil or sunflower oil;
saturated or unsaturated fatty acid esters or synthetic oils such as isopropyl or ethyl palmitate, diisopropyl adipate, alkyl myristates such as those of isopropyl, butyl and cetyl, hexyl stearate, cetyl ricin, oleate, stearyl octanoate (purcellin oil), cetyl/stearyl 2-ethylhexanoate, dioctyl malate, esters of $C_{12}-C_{18}$ fatty acids and polyols such as esters of these acids and of glycerol, for example the triglycerides of these fatty acids, as well as polyisobutene.

The oil phase of these emulsions according to the invention may also contain some waxes and especially carnauba wax, beeswax, ozocerite, candelilla wax and microcrystalline waxes, silicone oils, or $C_{12}-C_{18}$ fatty acids and fatty alcohols.

The aqueous phase of the emulsions according to the invention may also contain lower monoalcohols or polyalcohols containing 1 to 6 carbon atoms. The monoalcohols or polyalcohols particularly preferred are ethanol, isopropanol, propylene glycol and glycerine.

The emulsifiers are present either in the fatty phase or in the aqueous phase or in both phases at the same time.

The proportion of the emulsifiers is generally between 1 and 15% relative to the total weight of the emulsion.

These emulsifiers are chosen from among:
polyoxyethylenated alkyl ($C_8-C_{12}$) phenols containing 9 to 15 moles of ethylene oxide;
polyoxyethylenated $C_{12}-C_{18}$ fatty alcohols comprising at least 4 and preferably 4 to 35 moles of ethylene oxide;
polyglycerolated $C_{10}-C_{18}$ fatty alcohols comprising 4 to 10 glycerol residues;
polyoxypropylenated $C_{12}-C_{18}$ fatty alcohols preferably comprising 3 moles of propylene oxide;
$C_{12}-C_{18}$ fatty acid esters conjointly polyoxyethylenated and polyglycerolated or monoglycerolated;
polyoxyethylenated $C_{12}-C_{18}$ fatty acid esters of sorbitan containing 10 to 20 moles of ethylene oxide;
polyoxyethylenated $C_{12}-C_{18}$ fatty acid esters comprising at least 2 ethylene oxide residues and preferably 4 to 20 ethylene oxide residues;
polyoxyethylenated castor oil containing 10 to 60 moles of ethylene oxide;
· propylene oxide/ethylene oxide copolymers;
soybean or egg yolk lecithin;
sucroglycerides;
soaps;
fatty alcohol phosphoric esters;

fatty alcohol sulphates optionally oxyethylenated;

lanolin alcohols, polyoxyethylenated and comprising at least 4 ethylene oxide residues.

The emulsions according to the invention may also contain thickeners, emollients, humectants, surfaceactive agents, preservatives, antifoams, perfumes, dyes or pigments whose function is to dye the composition itself or the skin or to absorb or reflect solar radiation, or any other ingredient normally employed in cosmetics.

These emulsions may be provided in various forms such as a milk, a cream, and be prepared as aerosols.

These emulsions may optionally contain, in addition to the combination of the two screens according to the invention, other well-known water soluble or fat soluble UV screens such as for example coffee oil, salicylic acid derivatives, cinnamic acid derivatives, p-aminobenzoic acid esters and derivatives, anthranilates, benzophenone derivatives, benzylidenecamphor derivatives such as p-methylbenzylidenecamphor, dibenzoylmethane derivatives, benzotriazole derivatives, benzoxazole derivatives, benzimidazole derivatives and alkyl($C_2$-$C_{10}$) α-cyano-β,β-diphenylacrylates.

The invention will be better understood with the help of the following examples which do not limit the scope of the invention.

Preparation Examples

EXAMPLE 1

Preparation of a compound of general formula (I) in which A designates $M^{n+}/n$, $M^{n+}$ representing $Mg^{2+}$ 3 litres of water are added to 1 kg of an aqueous solution at 30% terephthalylidene dicamphorsulphonic acid (0.533 mole). 108 g (0.533 mole) of magnesium chloride, hexahydrate, are introduced with stirring and the stirring is maintained for 90 minutes.

The reaction mixture is filtered. The white solid obtained is washed with water under stirring, then with ethanol and dried under reduced pressure.

260 g of the expected product are thus obtained in the form of a white powder exhibiting the following properties:

Melting point: >300° C.

Elemental analysis: $C_{28}H_{32}O_8S_2Mg$, $5H_2O$

|  | C % | H % | O % | S % | Mg % |
|---|---|---|---|---|---|
| Calculated: | 49.81 | 6.27 | 30.81 | 9.49 | 3.60 |
| Found: | 51.14 | 6.57 | 29.51 | 8.67 | 4.11 |

EXAMPLE 2

Preparation of a compound of general formula (I) in which A designates $M^{n+}/n$, $M^{n+}$ representing $Zn^{2+}$ 700 cm³ of water are added to 200 g of an aqueous solution at 29.5% terephthalylidene dicamphorsulphonic acid (0.105 mole). 14.2 g (0.105 mole) of zinc chloride, dihydrate, in solution in 160 cm³ of water are introduced with stirring and the stirring is maintained for 3 hours.

The reaction mixture is filtered. The white solid is washed with water under stirring and dried under reduced pressure.

57 g of the expected product are thus obtained in the form of a white powder exhibiting the following properties:

Melting point: >300° C.

Elemental analysis: $C_{28}H_{32}O_8S_2Zn$, $6H_2O$

|  | C % | H % | O % | S % | Zn % |
|---|---|---|---|---|---|
| Calculated: | 45.78 | 5.99 | 30.52 | 8.72 | 8.86 |
| Found: | 45.30 | 6.03 | 31.09 | 8.68 | 9.11 |

EXAMPLE 3

Preparation of a compound of general formula (I) in which A designates $M^{n+}/n$, $M^{n+}$ representing $Al^{3+}$ 30 cm³ of water are added to 30 g of an aqueous solution at 29.5% terephthalylidene dicamphorsulphonic acid (0.016 mole). 2.41 g (0.013 mole) of aluminium chloride, trihydrate, in solution in 10 cm³ of water are introduced with stirring. 50 cm³ of water are added and the stirring is maintained for 3 hours.

The reaction mixture is filtered. The white solid obtained is washed with water under stirring and dried under reduced pressure.

8.4 g of the expected product are thus obtained in the form of a white powder exhibiting the following properties:

Melting point: >300° C.

Elemental analysis: $C_{84}H_{96}O_{24}S_6Al_2 \cdot 22H_2O$

|  | C % | H % | O % | S % | Al % |
|---|---|---|---|---|---|
| Calculated: | 47.28 | 6.57 | 34.50 | 9.00 | 2.53 |
| Found: | 46.71 | 6.46 | 31.96 | 8.84 | 2.43 |

EXAMPLE 4

Preparation of a compound of general formula (I) in which A designates $M^{n+}/n$, $M^{n+}$ representing $Ca^{2+}$ 100 cm³ of water are added to 100 g of an aqueous solution at 29.5% terephthalylidene dicamphorsulphonic acid (0.0525 mole). 7.7 g (0.0525 mole) of calcium chloride, dihydrate, in solution in 50 cm³ of water are added with stirring and the stirring is maintained for 1 hour.

The reaction mixture is filtered. The white solid obtained is washed with water under stirring and dried under reduced pressure.

27 g of the expected product are thus obtained in the form of a white powder exhibiting the following properties:

Melting point: >300° C.

Elemental analysis: $C_{28}H_{32}O_8S_2Ca$, $4H_2O$

|  | C % | H % | O % | S % | Ca % |
|---|---|---|---|---|---|
| Calculated: | 49.92 | 5.94 | 28.53 | 9.50 | 5.94 |
| Found: | 49.61 | 5.99 | 29.06 | 8.90 | 6.44 |

EXAMPLE 5

Preparation of a compound of general formula (I) in which A designates $M^{n+}/n$, $M^{n+}$ representing $Zr^{4+}$ 750 cm³ of water are added to 200 g of an aqueous solution at 29.5% terephthalylidene dicamphorsulphonic acid (0.106 mole). 12.3 g (0.053 mole) of anhydrous zirconium chloride dissolved in 925 cm³ of water are introduced with stirring and the stirring is maintained for 1 hour.

The reaction mixture is filtered. The white solid obtained is washed with water under stirring and dried under reduced pressure.

46.1 g of product are obtained in the form of a white powder exhibiting the following properties:

Melting point >250° C.

Weight Ratio between the carbon and the sulphur for:

$C_{56}H_{64}O_{16}S_4Zr$
Calculated: 5.25
Found: 5.20

Formulation Examples

EXAMPLE A

The following sun-protection composition is prepared:

| A - Fatty phase | |
|---|---|
| Lanolin | 7.0 g |
| Polyethoxylated oleic acid and glycerol ester sold under the name "LABRAFIL M 1969 CS" by the company GATTEFOSSE | 3.0 g |
| Glyceryl stearate and polyethylene glycol 100 stearate mixture sold under the name "ARLACEL 165" by the company ICI | 5.0 g |
| Silicone oil | 0.8 g |
| Cetyl alcohol | 3.0 g |
| Stearic acid | 2.5 g |
| Polyoxypropylenated myristyl alcohol containing 3 moles of propylene oxide sold under the name "WITCONOL APM" by the company WITCO | 7.5 g |
| Dioctyl malate sold under the name "CERAPHYL 45" by the company VAN DYCK | 7.5 g |
| Triethanolamine | 0.2 g |
| Potassium hexadecylphosphate sold under the name "AMPHISOL K" by the company GIVAUDAN | 0.5 g |
| 2,4,6-Tris[p-(2'-ethylhexyl-1'-oxycarbonyl)anilino]-1,3,5-triazine sold by the company BASF under the name "UVINUL T 150" | 3.0 g |
| Preservative, antioxidant qs | |
| TOTAL: | 40.2 g |
| B - Aqueous phase | |
| Benzene-1,4-[bis(3-methylidenecamphormethylsulphonic)] acid | 3.0 g AM |
| Triethanolamine | 1.8 g |
| Perfume, preservative qs | |
| Water | 54.2 g |

The emulsion is prepared by adding the fatty phase, heated to about 80° C., to the aqueous phase, heated to the same temperature and under rapid stirring. An oil-in-water emulsion in the form of a cream is obtained.

EXAMPLE B

The following sun-protection composition is prepared:

| A - Fatty phase: | |
|---|---|
| Cetylstearyl alcohol | 5.6 g |
| Polyoxyethylenated cetylstearyl alcohol containing 33 moles of ethylene oxide | 1.4 g |
| Non-autoemulsifiable glyceryl monostearate and distearate mixture | 2.0 g |
| Silicone oil | 1.5 g |
| Cetyl alcohol | 1.5 g |
| Polyoxypropylenated myristyl alcohol containing 3 moles of propylene oxide sold under the name "WITCONOL APM" by the company WITCO | 7.5 g |
| Dioctyl malate sold under the name "CERAPHYL 45" by the company VAN DYCK | 7.5 g |
| 2,4,6-Tris[p-(2'-ethylhexyl-1'-oxycarbonyl)anilino]-1,3,5-triazine sold by the company BASF under the name "UVINUL T 150" | 3.0 g |
| Preservative qs | |
| TOTAL: | 30.2 g |
| B - Aqueous phase | |
| Benzene-1,4-[bis(3-methylidenecamphormethylsulphonic)] acid | 3.0 g AM |
| Glycerin | 20.0 g |
| Triethanolamine | 1.8 g |
| Perfume, preservative qs | |
| Water | 44.2 g |

The emulsion is prepared by adding the fatty phase, heated to about 80° C., to the aqueous phase, heated to the same temperature and under rapid stirring. An oil-in-water emulsion in the form of a cream is obtained.

EXAMPLE C

The following sun-protection composition is prepared in the same manner as in Example A:

| A - Fatty phase: | |
|---|---|
| Cetylstearyl alcohol | 5.6 g |
| Polyoxyethylenated cetylstearyl alcohol containing 33 moles of ethylene oxide | 1.4 g |
| Non-autoemulsifiable glyceryl monostearate and distearate mixture | 2.0 g |
| Silicone oil | 1.5 g |
| Cetyl alcohol | 1.5 g |
| Dioctyl malate sold under the name nation "CERAPHYL 45" by the company VAN DYCK | 15.0 g |
| 2,4,6-Tris[p-(2'-ethylhexyl-1'-oxycarbonyl)anilino]-1,3,5-triazine sold by the company BASF under the name "UVINUL T 150" | 5.0 g |
| Glycerin | 20.0 g |
| Preservative, antioxidant qs | |
| TOTAL: | 52.2 g |
| B - Aqueous phase | |
| Benzene-1,4-[bis(3-methylidenecamphormethylsulphonic)] acid | 1.0 g AM |
| Triethanolamine | 0.6 g |
| Perfume, preservative qs | |
| Water | 45.4 g |

EXAMPLE D

The following sun-protection composition is prepared in the same manner as in Example A:

| A - Fatty phase: | |
|---|---|
| Cetylstearyl alcohol | 5.6 g |
| Polyoxyethylenated cetylstearyl alcohol containing 33 moles of ethylene oxide | 1.4 g |
| Non-autoemulsifiable glyceryl monostearate and distearate mixture | 2.0 g |
| Silicone oil | 1.5 g |
| Cetyl alcohol | 1.5 g |
| Diisopropyl adipate | 15.0 g |
| 2,4,6-Tris[p-(2'-ethylhexyl-1'-oxycarbonyl)anilino]-1,3.5-triazine sold by the company BASF under the name "UVINUL T 150" | 1.5 g |
| Glycerin | 20.0 g |
| Preservative, antioxidant qs | |
| TOTAL: | 48.7 g |
| B - Aqueous phase | |

| -continued | |
|---|---|
| Benzene-1,4-[bis(3-methylidenecamphor-methylsulphonic)] acid, aluminium salt | 5.1 g |
| Triethanolamine | 1.7 g |
| Perfume, preservative qs | |
| Water | 43.7 g |

I claim:

1. An ultraviolet radiation screening cosmetic emulsion which screens out wavelengths between 280 nm and 400 nm which comprises in an oil phase, an effective amount of 2,4,6-tris[p-(2'ethylhexyl-1'-oxycarbonyl)anilino-1,3,5-triazine and, in an aqueous phase, an effective amount of partially or fully neutralized benzene-1,4-acid of the formula:

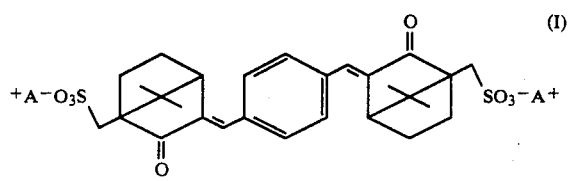

in which A designates a hydrogen atom, an alkali metal, a $N(R)_4^+$ group, R designating a hydrogen atom or a $C_1$-$C_4$ alkyl or hydroxyalkyl radical, or a $M^{n+}/n$ group where $M^{n+}$ is a polyvalent metal cation in which n is 2, 3 or 4.

2. A Cosmetic screening emulsion according to claim 1, which comprises 0.1 to 10% by weight, calculated on the basis of the acid, of benzene-1,4-[bis(3-methylidenecamphormethylsulphonic)]acid, partially or completely neutralised, and 0.1 to 10% by weight of 2,4,6-tris[p-(2'-ethylhexyl-1'-oxycarbonyl)anilino]-1,3,5-triazine.

3. A Cosmetic screening emulsion according to claim 1 which comprises 1 to 6% by weight, calculated on the basis of the acid, of benzene-1,4-[bis(3-methylidenecamphormethylsulphonic)] acid, partially of completely neutralised, and 1 to 6% by weight of 2,4,6-tris[p-(2'-ethylhexyl-1'-oxycarbonyl)-anilino]-1,3,5-triazine.

4. A Cosmetic screening emulsion according to claim 1, wherein the benzene-1,4-[bis(3-methylidenecamphormethylsulphonic)] acid is partially of completely neutralised by an alkali hydroxide, by ammonium hydroxide, by an alkanolamine or by a polyvalent metal salt or hydroxide of valency equal to 2 or 3 or 4, selected from the group consisting of calcium, zinc, magnesium, barium, aluminum and zirconium.

5. A Cosmetic screening emulsion according to claim 1, which is an oil-in-water emulsion the pH of which is between 4 and 9.

6. A cosmetic screening emulsion according to claim 1, wherein the oil phase consists of fatty substances selected from the group consisting of mineral oils, modified vegetable oils, unmodified vegetable oils, modified animal oils, unmodified animal oils, saturated fatty acid esters, unsaturated fatty acid esters, synthetic oils, waxes, silicone oils, and $C_{12}$-$C_{18}$ fatty acid and fatty alcohols.

7. A Cosmetic composition according to claim 1, wherein the aqueous phase comprises, in addition to water, a $C_1$-$C_6$ lower monoalcohol or polyalcohol.

8. A Cosmetic screening emulsion according to claim 1, which further contains an emulsifier in an amount of from 1 to 15% of the total weight of the emulsion.

9. A cosmetic screening emulsion according to claim 1, wherein the emulsifier is a member selected from the group consisting of a polyoxyethylenated alkyl ($C_8$-$C_{12}$) phenol containing from 9 to 15 moles of ethylene oxide; a polyoxyethylenated $C_{12}$-$C_{18}$ fatty alcohol containing at least 4 moles of ethylene oxide; a polyglycerolated $C_{10}$-$C_{18}$ fatty alcohol containing from 4 to 10 moles of glycerol; a polyoxypropylenated $C_{12}$-$C_{18}$ fatty alcohol; a polyoxyethylenated and polyglycerolated or monoglycerolated $C_{12}$-$C_{18}$ fatty acid ester; a polyoxyethylenated $C_{12}$-$C_{18}$ fatty acid ester of sorbitan containing from 10 to 20 moles of ethylene oxide; a polyoxyethylenated $C_{12}$-$C_{18}$ fatty acid ester containing at least 2 moles of ethylene oxide; a polyoxyethylenated castor oil containing from 10 to 60 moles of ethylene oxide; a propylene oxide/ethylene oxide copolymer; soybean or egg yolk lecithin; a sucroglycerides; a soap; a fatty alcohol phosphoric ester; an optionally oxyethylenated fatty alcohol sulphate; and a polyoxyethylenated lanolin alcohol, containing at least 4 moles of ethylene oxide.

10. A cosmetic screening composition according to claim 1, which further contains a member selected from the group consisting of thickener, emollient, humectant, surface-active, agent preservative, antifoam, perfume, dye, and pigment.

11. A Cosmetic screening emulsion according to claim 1, which is in the form of a milk, cream or aerosol.

12. A Cosmetic screening emulsion according to claim 1, which further comprises another water-soluble or fat-soluble UV screen selected from the group consisting of coffee oil, a salicylic acid derivative, a cinnamic acid derivative, a p-aminobenzoic acid ester or derivative, an anthranilate, a benzophenone derivative, a benzylidenecamphor derivative, a dibenzoylmethane derivative, a benztriazole derivative, a benzoxazole derivative, a benzimidazole derivative, and an alkyl ($C_2$-$C_{10}$) $\alpha$-cyano-$\beta,\beta$-diphenylacrylate.

13. Process for protecting the human epidermis against ultraviolet radiation of wavelengths between 280 and 400 nm, which comprises applying to the skin an effective amount of a cosmetic screening emulsion according to claim 1.

14. A Cosmetic emulsion according to claim 1, wherein $M^+$ is $Ca^{2+}$, $Zn^{2+}$, $Mg^{2+}$, $Ba^{2+}$, $Al^{3+}$, or $Zr^{4+}$.

15. A Cosmetic screening emulsion according to claim 12, wherein the benzylidenecamphor derivative is p-methylbenzylidenecamphor.

* * * * *